United States Patent
Lother et al.

(10) Patent No.: US 10,070,924 B2
(45) Date of Patent: Sep. 11, 2018

(54) APPARATUS AND METHOD PERTAINING TO A MULTI-TIER BACK-TABLE DRAPE

(71) Applicant: Medline Industries, Inc., Mundelein, IL (US)

(72) Inventors: Troy Lother, Kenosha, WI (US); Amanda Jaron, Chicago, IL (US)

(73) Assignee: Medline Industries, Inc., Northfield, IL (US)

( * ) Notice: Subject to any disclaimer, the term of this patent is extended or adjusted under 35 U.S.C. 154(b) by 957 days.

(21) Appl. No.: 13/800,695

(22) Filed: Mar. 13, 2013

(65) Prior Publication Data
US 2014/0261457 A1    Sep. 18, 2014

(51) Int. Cl.
*A61B 19/08*    (2006.01)
*A61B 46/10*    (2016.01)
*A61B 46/00*    (2016.01)

(52) U.S. Cl.
CPC ............ *A61B 19/081* (2013.01); *A61B 46/10* (2016.02); *A61B 46/40* (2016.02)

(58) Field of Classification Search
CPC .............. A61B 19/0248; A61B 19/081; A61B 2019/025; A61B 2019/0255; A61B 19/08; A61B 2019/085; A61B 19/10; A61B 2019/106; A61B 19/088; A61B 17/3431; A61B 17/0493; A61B 19/38; A61B 17/0293; A61B 19/087; A61F 13/15203; A61F 13/15699; A61F 13/4902; A61F 13/51401; A61F 13/51464; A61F 13/51476; A61F 13/51478; A61F 13/5148; A61F 13/62; A61F 2013/51429; A61F 15/005; A61F 2013/530131; B32B 27/12; B32B 5/26; A41D 13/04; A61G 13/102
(Continued)

(56) References Cited

U.S. PATENT DOCUMENTS 3,667,458 A    6/1972    Krebs
3,707,964 A    1/1973    Patience et al.
(Continued)

FOREIGN PATENT DOCUMENTS

CN    101496742    8/2009
CN    201602902    10/2010
(Continued)

OTHER PUBLICATIONS

U.S. Appl. No. 13/339,837, filed Dec. 29, 2011, entitled "Method and Apparatus Pertaining to a Medical Drape Having a Suction Port.".
(Continued)

Primary Examiner — Ophelia A Hawthorne
(74) Attorney, Agent, or Firm — Fitch, Even, Tabin & Flannery LLP (57) ABSTRACT

A drape suitable for use with a multi-tier back table has a first fabric portion configured to substantially cover a lower table surface and a second fabric portion configured as a pocket that receives at least a substantial portion of an upper table surface. By one approach this pocket includes at least one hand slot configured to receive a user's hand such that the user can lift the second fabric portion and slide the pocket over the upper table surface. A third fabric portion having a vertical panel connects the first and second fabric portions.

14 Claims, 6 Drawing Sheets

(58) Field of Classification Search
USPC .................................................. 128/849–856
See application file for complete search history.

(56) References Cited

U.S. PATENT DOCUMENTS

| | | | |
|---|---|---|---|
| 3,721,242 A | 3/1973 | Krusko | |
| 3,750,664 A | 8/1973 | Collins | |
| 3,791,381 A | 2/1974 | Krzewinski | |
| 3,799,161 A | 3/1974 | Collins | |
| 3,826,253 A | 7/1974 | Larsh | |
| 4,089,331 A | 5/1978 | Hartigan | |
| 4,169,472 A | 10/1979 | Morris | |
| 4,192,312 A | 3/1980 | Wilson | |
| D256,161 S | 7/1980 | Oliver | |
| 4,384,573 A | 5/1983 | Elliott | |
| 4,489,720 A | 12/1984 | Morris | |
| 4,559,937 A | 12/1985 | Vinson | |
| 4,586,498 A | 5/1986 | Morris | |
| 4,616,642 A | 10/1986 | Martin | |
| 4,798,201 A | 1/1989 | Rawlings | |
| 4,869,271 A | 9/1989 | Idris | |
| 4,944,737 A | 7/1990 | Bloom | |
| 5,042,507 A | 8/1991 | Dowdy | |
| 5,060,662 A | 10/1991 | Farnswoth, III | |
| 5,195,893 A | 3/1993 | Casale | |
| 5,209,243 A | 5/1993 | Glassman | |
| 5,345,946 A | 9/1994 | Butterworth et al. | |
| 5,464,024 A | 11/1995 | Mills | |
| D373,921 S | 9/1996 | Palomo | |
| 5,778,889 A | 7/1998 | Jascomb | |
| 5,778,890 A | 7/1998 | Lofgren | |
| 5,800,483 A | 9/1998 | Vought | |
| 5,875,780 A | 3/1999 | Rodriguez | |
| 5,991,666 A | 11/1999 | Vought | |
| 6,019,102 A * | 2/2000 | Becker | 128/849 |
| 6,032,670 A | 3/2000 | Miller | |
| 6,199,553 B1 | 3/2001 | Hafer | |
| 6,213,124 B1 | 4/2001 | Butterworth | |
| 6,314,958 B1 * | 11/2001 | Harroll et al. | 128/849 |
| 6,345,621 B1 | 2/2002 | Chandler et al. | |
| D467,345 S | 12/2002 | Gingles | |
| 6,497,233 B1 * | 12/2002 | DeAngelis | 128/849 |
| 6,612,310 B2 | 9/2003 | Sklar | |
| 6,694,981 B2 | 2/2004 | Gingles | |
| 6,725,864 B2 | 4/2004 | Ewonce | |
| 6,835,256 B2 * | 12/2004 | Menzies et al. | 156/62.4 |
| 6,843,252 B2 | 1/2005 | Harrison | |
| 6,923,186 B2 | 8/2005 | Gavette | |
| 7,086,404 B2 | 8/2006 | Dusenbery | |
| 7,588,034 B2 | 9/2009 | Mathis | |
| 7,752,768 B2 | 7/2010 | Young | |
| 7,853,311 B1 | 12/2010 | Webb | |
| 8,011,371 B2 | 9/2011 | Rotolo | |
| 8,079,365 B2 | 12/2011 | Block | |
| 8,459,265 B2 * | 6/2013 | Young et al. | 128/849 |
| D693,603 S | 11/2013 | Esquivel | |
| 8,783,262 B2 | 7/2014 | Carrez | |
| 8,967,150 B2 | 3/2015 | Carrez | |

| | | | |
|---|---|---|---|
| 2002/0174870 A1 | 11/2002 | Ewonce et al. | |
| 2003/0051362 A1 | 3/2003 | Buckman | |
| 2003/0187458 A1 | 10/2003 | Carlson | |
| 2004/0103903 A1 | 6/2004 | Falahee | |
| 2004/0118049 A1 | 6/2004 | Chen | |
| 2005/0234322 A1 | 10/2005 | Lober | |
| 2006/0219249 A1 | 10/2006 | Czajka | |
| 2008/0006279 A1 | 1/2008 | Bodenham | |
| 2009/0158487 A1 | 6/2009 | Paulsen | |
| 2009/0277460 A1 | 11/2009 | Carrez | |
| 2011/0015557 A1 | 1/2011 | Aali et al. | |
| 2011/0030702 A1 | 2/2011 | Czajka, Jr. | |
| 2011/0041995 A1 * | 2/2011 | Adams | 156/250 |
| 2011/0214679 A1 | 9/2011 | Chua | |
| 2011/0247634 A1 | 10/2011 | Young | |
| 2012/0017921 A1 | 1/2012 | Esquivel | |
| 2012/0222686 A1 | 9/2012 | Lockwood | |
| 2012/0298115 A1 | 11/2012 | Haines | |
| 2013/0304080 A1 | 11/2013 | Landry | |
| 2014/0012119 A1 | 1/2014 | Geaghan | |
| 2015/0135398 A1 | 5/2015 | Czajka | |
| 2015/0359596 A1 | 12/2015 | Jarrelle | |

FOREIGN PATENT DOCUMENTS

| | | |
|---|---|---|
| EP | 2151211 | 2/2010 |
| SU | 445412 A1 | 10/1974 |
| WO | 2011088326 | 7/2011 |
| WO | 2013036387 | 3/2013 |
| WO | 2014083573 | 6/2014 |

OTHER PUBLICATIONS

U.S. Appl. No. 13/410,058, filed Mar. 1, 2012, entitled "Surgical Drape with Selectively Detachable Barrier.".
International Search Report and Written Opinion; PCT Patent Application No. PCT/US2014/023215; dated Jul. 24, 2014.
Notification of the First Office Action dated Mar. 20, 2015 from Chinese Patent Application No. 2012800215110.
Australian Patent Application No. 2012223335; Patent Examination Report No. 1; dated Aug. 14, 2015; 4 pages.
Canadian Patent Application No. 2,832,104; Office Action dated Aug. 12, 2015; 5 pages.
Article 94(3) EPC from European Patent Application No. 12751757.1 dated Jan. 5, 2017; 7 pages.
International Search Report and Written Opinion from PCT/US2017/022278 dated Jun. 19, 2017; 11 pages.
International Search Report and Written Opinion from PCT/US2017/022450 dated Jun. 7, 2017; 12 pages.
Extended European Search Report from European Patent Application No. 17173255.5 dated Aug. 18, 2017; 10 pages.
Australian Patent Application No. 2012223335; Patent Examination Report No. 2; dated Aug. 15, 2016; 6 pages.
Chinese Patent Application No. 2012800215110; Office Action dated Mar. 20, 2015 with English translation.
Chinese Patent Application No. 2012800215110; Office Action dated Nov. 4, 2015 with English translation.

* cited by examiner

APPARATUS AND METHOD PERTAINING TO A MULTI-TIER BACK-TABLE DRAPE

TECHNICAL FIELD

This invention relates generally to sterile drapes and more particularly to sterile drapes for multi-tier back tables.

BACKGROUND

Many medical surgical procedures presume a clean operating environment. For example, the technicians and medical-services providers in the operating environment are typically garbed in antiseptic gowns, gloves, foot coverings, face masks, and so forth. Hand tools and other equipment and supplies pertinent to the procedure are similarly sterile.

In many cases, various artifacts to be used during the procedure are arrayed on a support surface such as a table that is positioned convenient to the attending medical personnel during the procedure. These tables are often known as "back tables." To avoid sterilizing these back tables (or, in the alternative, to avoid using a new, sterile, one-time-use back table) attending medical personnel typically place a sterile drape over the back table. Hand tools and other equipment and supplies can then be placed atop the drape without contaminating those artifacts.

Some back tables have multiple tiers to provide greater surface area without increasing the back table's required floor space requirements. Specially-designed drapes are available to cover each horizontal surface of such a multi-tier back table. While effective for the intended purpose when properly deployed, such multi-tier back-table drapes can be confusing to properly deploy. Confusion in these regards, in turn, increases the risk that the technicians deploying the drape will inadvertently contaminate a surface of the drape that should remain clean.

Prior art approaches in these regards also typically always require at least two technicians to properly deploy the drape. This requirement can divert scarce personnel from other important tasks (thus extending cycle time for the procedure) and/or can cause more people to be assigned in support of a given procedure than might otherwise be necessary.

Accordingly, prior art approaches can pose risk to compromising the sterility of the operating environment and/or can contribute to increased overhead costs for supported procedures.

BRIEF DESCRIPTION OF THE DRAWINGS

The above needs are at least partially met through provision of the apparatus and method pertaining to a multi-tier back-table drape described in the following detailed description, particularly when studied in conjunction with the drawings, wherein.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, these various embodiments present a drape suitable for use with a multi-tier back table, the table having a lower table surface and an upper table surface. The drape comprises a first fabric portion configured to substantially cover the lower table surface and a second fabric portion configured as a pocket that receives at least a substantial portion of the upper table surface. By one approach this pocket includes at least one hand slot configured to receive a user's hand such that the user can lift the second fabric portion and slide the pocket over the upper table surface. A third fabric portion comprising a vertical panel connects the first and second fabric portions.

By one approach the foregoing first, second, and third fabric portions are all comprised of a single (i.e., contiguous and unseparated) fabric sheet. The fabric sheet itself can be comprised, for example, of a spunbound polyethylene material. Padding material can be added to supplement the single fabric sheet as desired. For example, a portion of the first fabric portion and the upper surface of the pocket can both include padding to thereby offer a padded surface atop the lower table surface and the upper table surface.

These teachings will also accommodate including helpful instructional content on the drape to instruct the user with respect to proper deployment of the drape on the aforementioned multi-tier back table. This instructional content can serve, for example, to provide instructions regarding a sequential order by which the first fabric portion is first unfolded to overhang a front portion of the lower table surface before the first fabric portion is then unfolded to overlie a rear horizontal portion of the lower table surface. Observing this sequence can help the user avoid accidentally contaminating the outer surface of the first fabric portion by helping the user to avoid contaminating themselves during the drape-deployment activity.

The aforementioned hand slot can comprise a plurality of hand slots if desired. For example, the pocket of the second fabric portion can include four such hand slots if desired. So configured, the hands of the user (or users) can be placed in these hand slots such that the user can readily and easily lift the second fabric portion and slide the pocket over the upper table surface. Depending upon the width of the multi-tier back table, in many cases a proper deployment of the drape only requires a single technician.

These teachings will also accommodate, if desired, a lift fastener configured to simultaneously lift the underside material of the pocket and the third fabric portion as well. There can be two such lift fasteners, if desired, on opposing lateral sides of the pocket. The free ends of these lifting straps can selectively attach to the upper surface of the pocket to maintain the aforementioned lifting functionality.

So configured, a drape can be readily deployed on a multi-tier back table by, in many cases, only a single person. By judicious use of helpful instructional content a technician will typically be able to successfully deploy the drape with only a modicum of training, if that. These teachings can be implemented in a highly economical manner and yield a drape that, although easily deployed, will tend to remain in a deployed state. These teachings are highly scalable as well and will accommodate a variety of differently-shaped and differently-sized multi-tier back tables.

Figure 1:
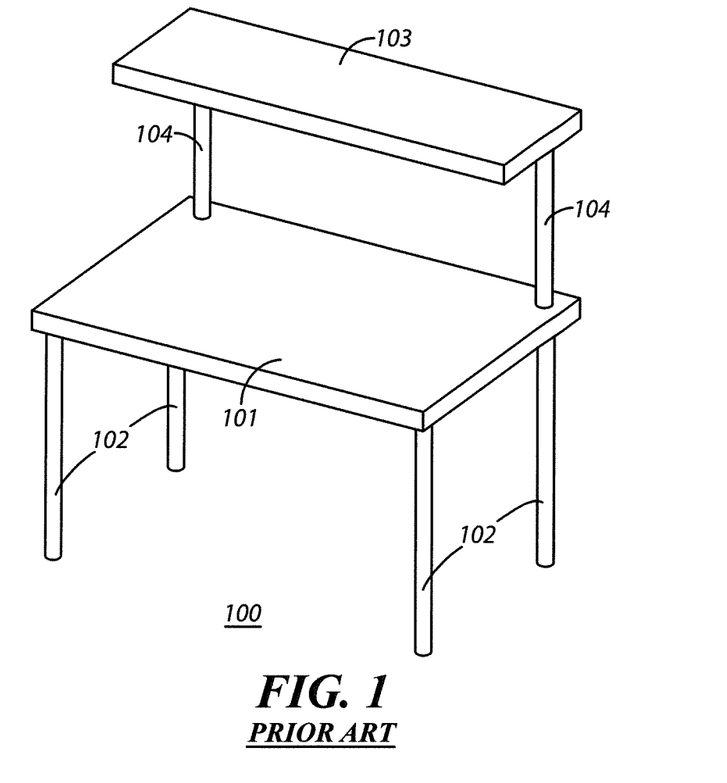
FIG. 1 comprises a perspective view as configured in accordance with the prior art.

These and other benefits may become clearer upon making a thorough review and study of the following detailed description. Referring now to the drawings, FIG. 1 presents a simple illustrative example of a multi-tier back table (more specifically, a two-tier back table 100). This two-tier back table 100 has a lower table surface 101 supported, in this case, by four legs 102. An upper table surface 103 is disposed above the lower table surface 101 by a pair of legs 104. In this particular example that pair of legs 104 attaches near the back end of the upper table surface 103 such that the latter cantilevers forwardly.

Such a two-tier back table 100 may be comprised of a variety of materials such as one or more metals and/or plastic materials. The dimensions of such a two-tier back table 100 can vary as well, with the lower table surface 100 having a length that often varies from about two feet to around eight feet. The lower table surface 100 will have a height above the floor ranging typically from between three feet and five feet, with the upper table surface 103 often being another one to four feet above the lower table surface 101.

Those skilled in the art will recognize that one multi-tier back table can vary from another with respect to any number of design variables. It will accordingly be understood that the multi-tier back table shown in FIG. 1 is intended to only serve in an illustrative capacity and that the present teachings are in fact readily used with a wide variety of multi-tier back tables.

Figure 2:
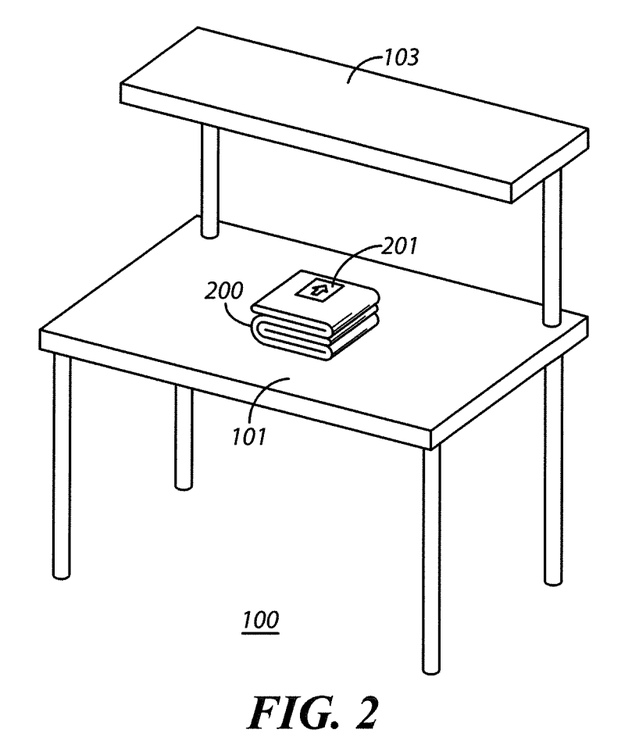
FIG. 2 comprises a perspective view as configured in accordance with various embodiments of the invention.

Referring to FIG. 2, the present teachings presume the use of a drape 200 that is folded and packaged by the manufacturer in a sterile state (using, for example, a sealed plastic bag). At a time of need the user opens that package and places the folded drape 200 on the lower table surface 101 of the two-tier back table 100. In this example the user places the folded drape 200 more or less in the middle of the lower table surface 101.

Figure 3:
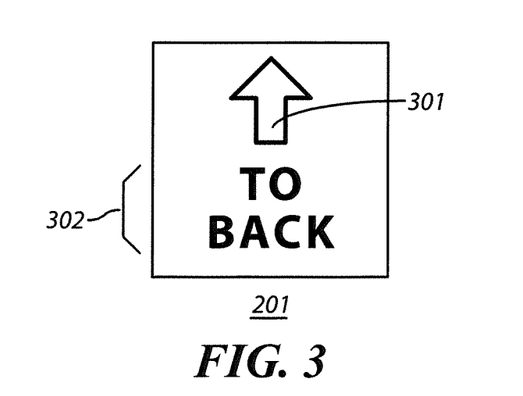
FIG. 3 comprises a top plan detail view as configured in accordance with various embodiments of the invention.

To help the user place the folded drape 200 with the correct side up and with a correct orientation vis-à-vis the lower table surface 101, instructional content 201 can be attached to the drape 200. As shown in FIG. 3, this instructional content 201 can comprise, by one approach, a sticker or other label that is secured to the drape 200. The instructional content 201 in this example includes an arrow 301 and the words "TO BACK" 302. Presuming that the other side of the folded drape 200 is lacking any such indicia, this instructional content 201 helps a user to recognize both that the side of the folded drape 200 that should be face up when placed on the lower table surface 100 and also that the folded drape 200 should be placed such that the arrow 301 points towards the back of the two-tier back table 100.

If desired, instead of a sticker, label, or the like, the instructional content 201 can be directly placed on the drape 200 using, for example, an ink-based printing approach. These teachings will accommodate using a variety of colors and other eye-attracting symbols, font, or the like to catch the attention of the user while also imparting useful information regarding, for example, proper placement of the drape and/or a next step in a sequence of drape-deployment steps as desired.

Figure 4:
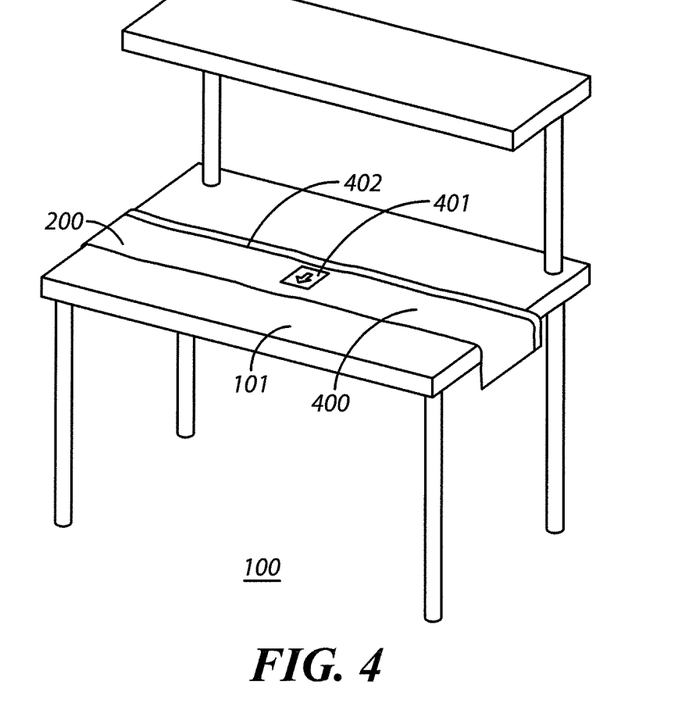
FIG. 4 comprises a perspective view as configured in accordance with various embodiments of the invention.

FIG. 4 depicts the drape 200 in a partially unfolded state. In particular, the drape 200 has been unfolded sideways to the left and to the right to reach its full length. The unfolded drape 200 exposes, at least in part, a first fabric portion 400 thereof. In this illustrative example the first fabric portion 400 serves the general purpose, when fully deployed, of at least substantially covering the lower table surface 101. For example, when fully deployed the first fabric portion 400 will cover at least eighty percent of the lower table surface 101 if not more.

Initially unfolding a table drape as shown in FIG. 4 is similar to at least some prior art practices in these regards. It is at this point during deployment of the drape when a user is at risk of contaminating themselves and then passing that contamination on to the drape itself. In particular, if the user should now unfold the drape towards the rear of the lower table surface 101, the user may well lean forward to the point that their gown comes in contact with portions of the two-tier back table 100. Since the two-tier back table 100 may be contaminated with microbes or other contaminants, such contact permits such contaminants to pass to the user's clothing. Those contaminants can then pass from the user's clothing back to the drape (or other clean surfaces) by way of further, subsequent contact.

Figure 5:
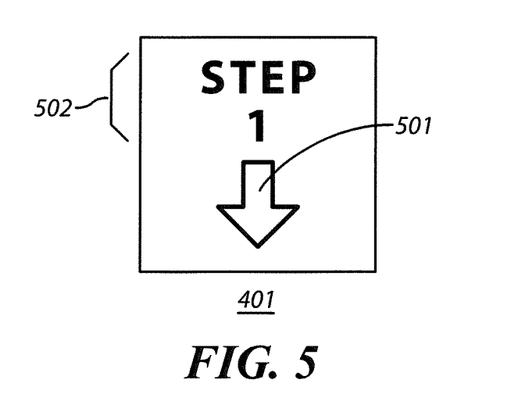
FIG. 5 comprises a top plan detail view as configured in accordance with various embodiments of the invention.

To help avoid such a circumstance and result, in this example the drape 200 includes another example of instructional content 401 that is located near an edge of the first fabric portion 400. Referring to FIG. 5, in this example that instructional content 401 includes an arrow 501 and the words "STEP 1" 502. The arrow can point towards the front of the two-tiered back table 100. Taken together, this instructional content 401 serves to attract the user's eye and attention and to clearly and unambiguous help the user understand that the next unfolding action should be to unfold the drape 200 forward to overhang a front portion of the lower table surface 101 before the first fabric portion 400 is unfolded to overlie a rear horizontal portion of the lower table surface 101.

Figure 6:
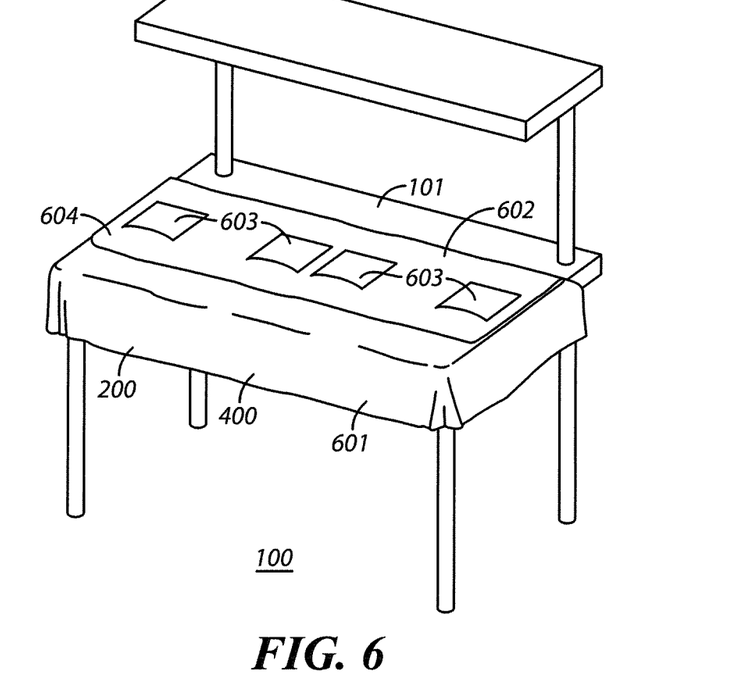
FIG. 6 comprises a perspective view as configured in accordance with various embodiments of the invention.

FIG. 6 depicts the results of the desired unfolding action. In particular, a front portion 601 of the first fabric portion 400 has been unfolded forward and now overhangs the front portion of the lower table surface 101. Accordingly, if the user should now happen to bump the multi-tier back table 100 while attending to the remaining deployment of the drape 200, the user's clean clothing will contact the clean drape 200 instead of the uncovered back table and contamination opportunities as described above are avoided.

FIG. 6 also depicts, in part, a second fabric portion 602 and a third fabric portion 604 that also comprise a part of the drape 200. By one approach the first, second, and third fabric portions 400, 602, and 604 can all comprise a single fabric sheet (that is, a single integral, contiguous sheet as versus, say, three portions that were cut from the same initial sheet (or from differing sheets altogether) and which were then reconnected to one another.

Figure 7:
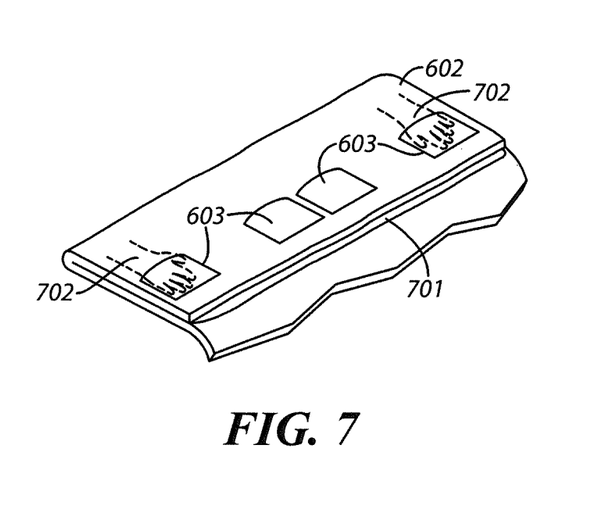
FIG. 7 comprises a perspective detail view as configured in accordance with various embodiments of the invention.

Referring to FIG. 7, the second fabric portion 602 is configured as a pocket 701 that can receive at least a substantial portion (say, at least eighty percent, or ninety percent, or some other significant portion of choice) of the upper table surface 103. By one approach this pocket 701 is formed by folding the second fabric portion 602 back on itself as illustrated and attaching the adjacent side edges to one another using any desired attachment mechanism (such as a suitable adhesive, staples or thread, brads or snaps, hooks-and-loops fasteners, magnets, and so forth).

As shown in both FIGS. 6 and 7, this pocket assembly can further include at least one hand slot 603. In this particular example the pocket assembly includes four discrete hand slots 603, with the two central hand slots 603 being disposed proximal to one another (for example, up to four inches apart), the two outer hand slots 603 being disposed relatively proximal to the edges of the pocket assembly, and all of the hand slots 603 being disposed at least substantially collinear with one another.

Figure 8:
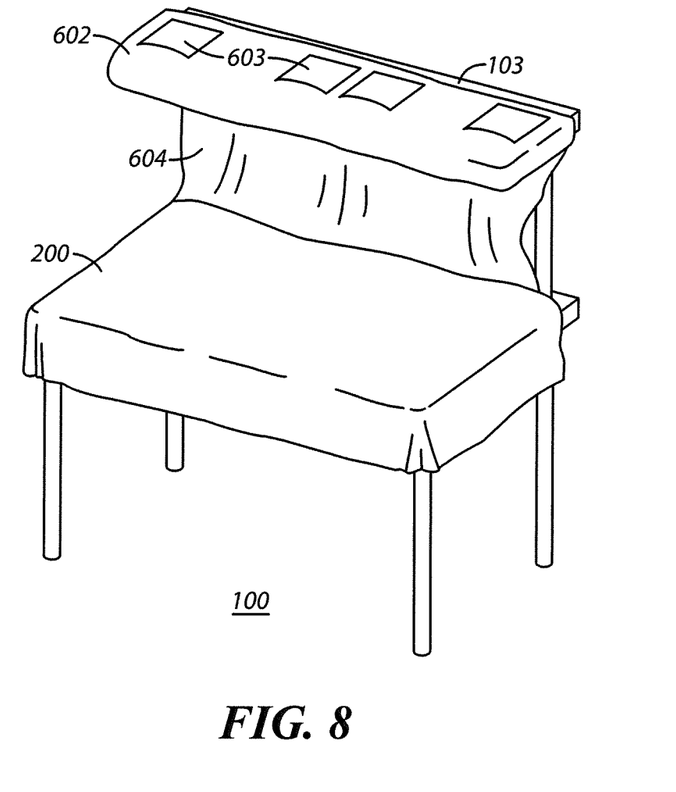
FIG. 8 comprises a perspective view as configured in accordance with various embodiments of the invention.

By their size, location, and orientation these hand slots 603 are configured to receive a user's hand 702 such that the user can lift the second fabric portion 602 and slide the pocket 701 over the upper table surface 103 as shown in FIG. 8. The fit of the pocket 701 about the upper table surface 103 can be as snug or as loose as may be desired and by one approach the pocket assembly signals to the user that this deployment step is complete by impeding further rearward movement when the upper table surface 103 reaches the end of the pocket 701.

In some cases a single user may be able to satisfactorily dispose the pocket 701 about the upper table surface 103 by placing their right and left hands into the outboard hand slots 603. When the two-tier back table 100 is sufficiently long so as to require a two-person deployment, the first person can place their hands in the two left-side hand slots 603 and the second person can place their hands in the two right-side hand slots 603. These two people, with a modicum of coordinated action, can then jointly lift the second fabric portion 602 as described above in order to slide the upper table surface 103 within the pocket 701.

These teachings will accommodate a variety of approaches with respect to forming these hand slots 603. As one example, each hand slot 603 can comprise a strip of material that attaches at its opposing ends to the second fabric portion 602 such that a user's hand can slide underneath the strip of material. As another example, such a swatch of material can be secured to the second fabric portion 602 on three of its sides to thereby form a hand-receiving pocket. As yet another example, slits can be formed partly or fully through the second fabric portion 602 to receive the user's hands as described.

Figure 9:
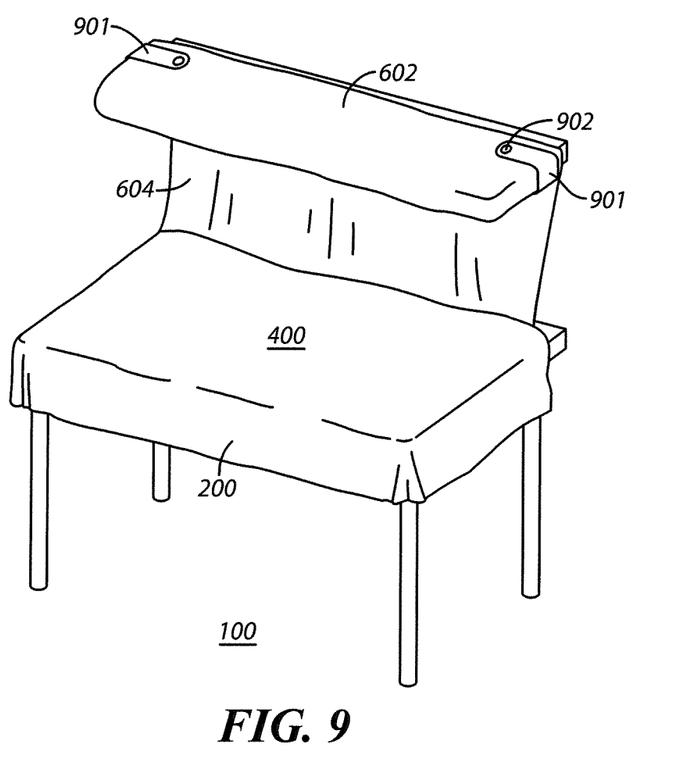
FIG. 9 comprises a perspective view as configured in accordance with various embodiments of the invention.

In some cases, and as suggested by the illustration presented at FIG. 8, the third fabric portion 604, which generally serves as a vertical panel that connects the first fabric portion 400 to the second fabric portion 602, may be somewhat loose. It is also possible that the second fabric portion 602 will be only loosely disposed about the upper table surface 103. Lift fasteners 901 as shown in FIG. 9 can serve to address one or both of these concerns.

By one approach these lift fasteners 901 comprise lifting straps that are disposed on opposing lateral sides of the pocket assembly (for example, towards the boundary between the second fabric portion 602 and the third fabric portion 604). The free ends of the lifting straps can, in turn, be provided with an attachment mechanism such as (but not limited to) a snap mechanism 902. So configured, a user can pull each lift fastener 901 taut and secure the lift fasteners 901 in a taut state by attaching the free ends of the lifting straps via the snap mechanisms 902 to counterpart attachment mechanisms on the pocket assembly. (For the sake of simplicity and clarity, FIG. 9 does not include a depiction of the aforementioned hand slots. In fact, it is anticipated that a drape 200 can include both the described hand slots and the described lift fasteners.)

By use of these lift fasteners 901 the pocket assembly can be closed more tightly around the upper table surface 103 to thereby aid in holding the pocket assembly in the deployed state. Such lift fasteners 901 can also serve to tighten the presentation of the vertical panel that is comprised of the third fabric portion 604. The lift fasteners 901 can be easily and readily unsnapped (or otherwise unsecured) when it is time to remove and dispose of the drape 200.

So configured, a one-piece drape 200 can be readily, easily, reliably, safely, and conveniently deployed on a corresponding multi-tier back table by, in many cases, only a single person.

Figure 10:
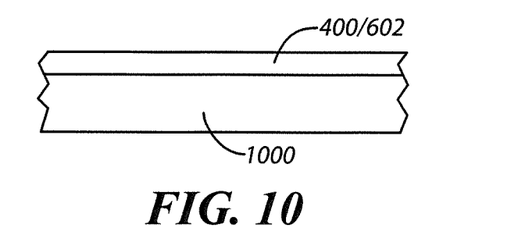
FIG. 10 comprises a side elevational detail view as configured in accordance with various embodiments of the invention.

These teachings are highly flexible in practice. As noted, the first, second, and third fabric portions can all be comprised of a single contiguous fabric sheet if desired (including the pocket assembly). That fabric sheet can comprise, for example, a spunbound material of choice or any other material as may suit the needs of a given application setting. As another example of the flexibility of these teachings, part or all of the drape 200 may comprise a laminate assembly as shown in FIG. 10. By way of illustration, portions of the first and second fabric portions 400 and 602 can comprise the aforementioned spunbound material and a second layer of padding material 1000 can be secured thereto. It can be useful, for example, to provide such padding material in portions of the first fabric portion 400 that are substantially coextensive with the horizontal surface of the lower table surface 101 and in upper portions of the pocket assembly.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

We claim:

1. A drape for use with a multi-tier back table having a lower table surface and an upper table surface, the drape comprising:
    a first fabric portion configured to substantially cover the lower table surface;
    a second fabric portion configured as a pocket that receives at least a substantial portion of the upper table surface, the pocket further including four hand slots configured to receive a user's hand such that the user can lift the second fabric portion and slide the pocket over the upper table surface, wherein all four of the hand slots are disposed colinear to one another and wherein first and second ones of the hand slots are centrally located laterally on the pocket and are spaced no more than four inches apart from one another and third and fourth ones of the hand slots are located on opposing sides of the pocket proximal to the edges of the pocket;
    a third fabric portion configured as a vertical panel that connects the first fabric portion to the second fabric portion.

2. The drape of claim 1 wherein the first fabric portion, the second fabric portion, and the third fabric portion are all comprised of a single fabric sheet.

3. The drape of claim 2 wherein at least portions of the single fabric sheet further include padding material.

4. The drape of claim 3 wherein at least a portion of the first fabric portion and a portion of the second fabric portion include the padding material.

5. The drape of claim 2 wherein the single fabric sheet comprises a spunbound material.

6. The drape of claim 1 further comprising:
a lift fastener configured to lift underside material of the pocket and the third fabric portion.

7. The drape of claim 6 wherein the lift fastener includes lifting straps disposed on opposing lateral sides of the pocket.

8. The drape of claim 7 wherein free ends of the lifting straps are selectively secured to an upper surface of the pocket.

9. The drape of claim 1 further including:
instructional content attached to the drape to instruct a user with respect to proper deployment of the drape on a multi-tier back table.

10. The drape of claim 9 wherein the instructional content includes instructions regarding a sequential order by which the first fabric portion is first unfolded to overhang a front portion of the lower table surface before the first fabric portion is then unfolded to overlie a rear horizontal portion of the lower table surface.

11. A method of forming a drape configured for use with a multi-tier back table having a lower table surface and an upper table surface, the method comprising:
providing a fabric sheet;
forming, at one end of the fabric sheet, a pocket sized and configured to receive the upper table surface;
forming four hand slots on the pocket sized and configured to receive a user's hand, wherein all four of the hand slots are disposed colinear to one another and wherein first and second ones of the hand slots are centrally located laterally on the pocket and are spaced no more than four inches apart from one another and third and fourth ones of the hand slots are located on opposing sides of the pocket proximal to the edges of the pocket;
wherein a remaining portion of the fabric sheet is of sufficient size to at least overlay at least a substantial portion of the lower table surface.

12. The method of claim 11 wherein the fabric sheet comprises a laminate assembly.

13. The method of claim 12 wherein at least one of layer of the laminate assembly comprises a spunbound material.

14. The method of claim 11 further comprising:
attaching at least one lift fastener to the fabric sheet proximal to the pocket.

* * * * *